United States Patent
Ko et al.

(10) Patent No.: US 9,844,523 B2
(45) Date of Patent: Dec. 19, 2017

(54) LACTIC ACID-CONTAINING COMPOSITION FOR INDUCING ANIMAL OVARIAN DYSFUNCTION

(71) Applicant: NAVIBIOTECH CO. LTD., Chungcheongnam-do (KR)

(72) Inventors: Jung Moon Ko, Gyeonggi-do (KR); Jun Jeong, Gyeonggi-do (KR); Ki Se Lee, Gyeonggi-do (KR)

(73) Assignee: Navibiotech Co. Ltd., Chungcheongnam-Do (KR)

( * ) Notice: Subject to any disclaimer, the term of this patent is extended or adjusted under 35 U.S.C. 154(b) by 179 days.

(21) Appl. No.: 14/400,489

(22) PCT Filed: Jan. 10, 2014

(86) PCT No.: PCT/KR2014/000302
§ 371 (c)(1),
(2) Date: Nov. 11, 2014

(87) PCT Pub. No.: WO2015/076455
PCT Pub. Date: May 28, 2015

(65) Prior Publication Data
US 2016/0271084 A1 Sep. 22, 2016

(30) Foreign Application Priority Data

Nov. 21, 2013 (KR) .................. 10-2013-0142018

(51) Int. Cl.
*A61K 31/19* (2006.01)
*A61K 9/00* (2006.01)
*A61K 47/02* (2006.01)
*A61K 47/42* (2017.01)
*A61K 47/12* (2006.01)

(52) U.S. Cl.
CPC ............ *A61K 31/19* (2013.01); *A61K 9/0019* (2013.01); *A61K 47/02* (2013.01); *A61K 47/12* (2013.01); *A61K 47/42* (2013.01)

(58) Field of Classification Search
None
See application file for complete search history.

(56) References Cited

U.S. PATENT DOCUMENTS 7,189,406 B1 * 3/2007 Gross ................ A61K 8/0208
424/401

FOREIGN PATENT DOCUMENTS

| GB | 2126478 | * | 3/1984 |
| KR | 10-2007-0041658 | | 4/2007 |
| KR | 10-1254705 B1 | | 4/2013 |

OTHER PUBLICATIONS

Troupe et al. In Industrial and Engineering Chemistry, 43(5), 1143-1146 (1951).*
Acid Dissociation Constants' in http://web.archive.org/web/20101129013823/http://preparatorychemistry.com/Bishop_weak_acid_Equilibrium.htm (2010) (retrieved from the internet Dec. 2, 2016).*
Deionized vs Distilled Water in https://www.leaf.tv/articles/deionized-vs-distilled-water/ (retrieved from the internet Dec. 2, 2016).*
Water for Injection (WFI) in cellgro.com/media/upload/file/productinfosheets/new/Water-for-Injection%20Quality%20Water.pdf (2012) (retrieved from the internet May 10, 2017).*

* cited by examiner

*Primary Examiner* — Dennis Heyer
(74) *Attorney, Agent, or Firm* — Kramer Amado, P.C.

(57) ABSTRACT

Disclosed is a lactic acid-containing composition for inducing animal ovarian dysfunction, designed to increase meat production by causing ovarian dysfunction within animals. The composition comprises 10 to 90% by weight of lactic acid and 10 to 90% by weight of an adjuvant, having a pH of 1~5. When locally injected into the ovary, the composition causes the ovarian tissue to lose its function, suppressing the estrus of the animals that thus improve in growth and appetite, with a consequent increase in meat production. Also, because even one injection of the lactic acid-based composition at a small dose can accomplish ovarian dysfunction, no lactic acid is left in the meat as well as the animals. Moreover, the composition, even though administered, does not require a drug-free interval, nor cause an increase in blood lactic acid level, and thus can produce animal products suitable for hormone-free certification.

6 Claims, 9 Drawing Sheets

LACTIC ACID-CONTAINING COMPOSITION FOR INDUCING ANIMAL OVARIAN DYSFUNCTION

TECHNICAL FIELD

The present invention relates to a lactic acid-containing composition for inducing animal ovarian dysfunction, designed to increase meat production by causing ovarian dysfunction within animals such as cow or pigs.

BACKGROUND ART

Forced disruption of the ovarian function of animals such as cows or pigs is known to suppress the estrus cycle of the females, bringing about an improvement in their growth rate and appetite and thus increasing meat production.

For ovarian dysfunction, ovariectomy is conventionally performed on female animals. In this case, the operation scar resulting from an abdominal incision degrades the commercial value and quality of meat of the female animals. Also, ovariectomized animals are difficult to manage in terms of postoperative rehabilitation for the prevention of inflammation of incision sites. Further, an ovariectomy cost, which is generally high, is negatively influential in terms of the economy of meat production.

Alternatively, a progesterone-based agent for inhibiting ovulation and follicular maturation may be fed, together with fodder, to animals to inhibit ovarian function. However, this strategy is imparted with a continuous burden of drug expense, and thus is economically ineffective. Also, the feeding of such hormone inhibitors results in the presence of hormonal ingredients, so that the meat product cannot be given hormone-free certification.

The equipment disclosed in Korean Patent Application Unexamined Publication No. 10-2007-0041658 (entitled "Equipment of myolysis using laser", hereinafter referred to as "Reference 1"), may be utilized to stop ovarian function, without an abdominal incision. In this regard, the sharp-pointed tip of the equipment may be allowed to penetrate into the functional tissue of the ovary, with the subsequent introduction of a drug, instead of laser, to the ovary. However, this method is cumbersome because it requires an ultrasonic machine and a camera for securing a view for operation, as well as an ingress guiding instrument. Further, the method is burdened with a cost of performing various processes with the instrument, causing an increase in the production cost of meat. Consequently, Reference 1 is difficult to apply in practice.

In order to overcome these disadvantages, the present inventor suggested a device as disclosed in Korean Patent No. 10-1254705 (entitled "Medicine injection device for animal ovary deactivation", hereinafter referred to as "Reference 2").

As shown in FIG. 1, the device comprises a catheter to a front portion of which a stopper is fixedly coupled and to a rear portion of which a needle-equipped communication tube is inserted, with a piston placed within the communication tube. The communication tube is also provided with a stopping ring at a rear side thereof, and a stopper is provided at a rear side of the catheter. The piston within the communication tube is connected with a thumb rest through a connection rod.

Having the aforementioned structure, the device of Reference 2 can allow the needle to safely reach a functional ovarian tissue, and thus functions as a device by which a drug for introducing ovarian dysfunction can be conveniently and economically injected. The device of Reference 2 is structured such that the needle is confined within the catheter until the catheter precisely reaches the functional tissue of the ovary. When reaching the functional tissue, the needle is extended from the catheter and penetrates into the functional ovarian tissue by a simple operation. In this position, the drug for introducing ovarian dysfunction is injected by pressing the thumb rest. Subsequently, the needle is retracted and the catheter is entirely withdrawn to finish the operation conveniently and economically.

Thus, Reference 2 can suppress the estrus of female animals, with the consequent advantages of improving growth rate and appetite, increasing meat productivity, avoiding post-operative problems, such as degradation of quality of meat resulting from abdominal incision, a burden of high operative cost and post-operative care, etc., and overcoming the problems encountered with the long-term administration of ovulation and follicular maturation inhibitors in terms of cost and hormone-free certification.

Since not necessitating various instruments including ultrasonic devices, Reference 2 can prevent an increase in the production cost of meat in addition to helping the operation be safe and simple.

Accordingly, a composition for inducing ovarian dysfunction that is applicable to the device of Reference 2 is required. So far, no ovarian dysfunction-inducing compositions that guarantee the safety of meats as foods and which prevent the degradation of quality of meats have been known. There is therefore a need for a composition for inducing ovarian dysfunction that is applicable to the device of Reference 2 and which allows the meat to be produced with high quality and which is safe for ingestion.

DISCLOSURE

Technical Problem

It is an object of the present invention to provide a lactic acid-based composition for inducing ovarian dysfunction, applicable to the device of Reference 2, which incurs neither inhibitory activity against the growth of animals nor degrades the quality and safety of meats as foods when it is injected into the functional tissue of the ovary.

Technical Solution

In order to accomplish the object, the present invention provides a lactic acid-based composition for inducing ovarian dysfunction, comprising 10 to 90% by weight of lactic acid and 10 to 90% by weight of an adjuvant.

Advantageous Effects

When locally injected into the ovary, as described hitherto, the composition of the present invention causes the ovarian tissue to lose its function, suppressing the estrus of the animals that thus improve in growth and appetite, with a consequent increase in meat production.

In addition, because even one injection of the lactic acid-based composition at a small dose can accomplish ovarian dysfunction, no lactic acid is left in the meat as well as the animals. Moreover, the composition for inducing ovarian dysfunction in accordance with the present invention, even administered, does not require a drug-free interval, nor cause an increase in blood lactic acid level, and thus can produce animal products suitable for hormone-free certification.

BEST MODE

Figure 1:
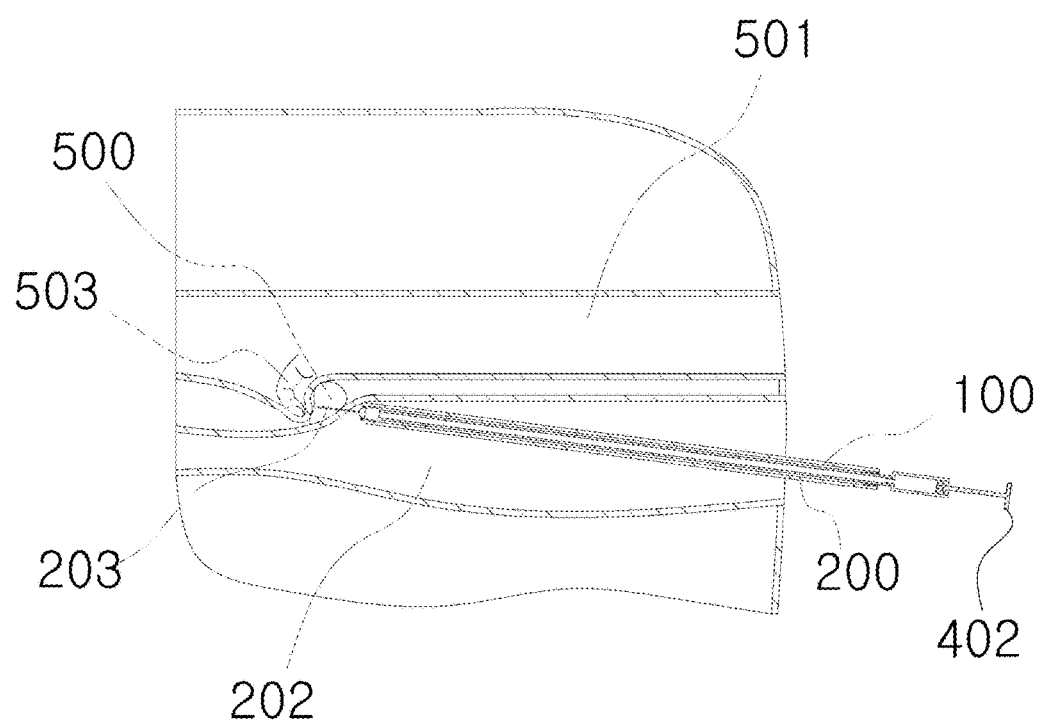
FIG. 1 is a view illustrating a device for injecting a drug for inducing ovarian dysfunction, devised by the present inventor.

The present invention is concerned with a composition for inducing ovarian dysfunction that comprises 10% to 90% by weight of lactic acid, sodium lactate, or calcium lactate; and 10% to 90% by weight of an adjuvant, wherein the composition is maintained at a pH of 1~5.

MODE FOR INVENTION

Reference should now be made to the drawings, in which the same reference numerals are used throughout the different drawings to designate the same or similar components.

The composition for inducing ovarian dysfunction according to the present invention is designed to be introduced to functional ovarian tissue by direct injection. This injection can be conducted with the aid of the device of FIG. 1. As the thumb rest 402 provided at a rear side of the communication tube 200 is pulled in a rear direction, the communication tube 200 moves toward the rear side of the catheter so that the needle 203 inserted into a front end of the communication tube 200 is confined within the catheter 100. After separation from the communication tube, the syringe 400 is filled with an injection solution and then engaged at its lower end to the communication tube 200. In this condition, the thumb rest 402 of the syringe 400 is pushed so that air is excavated from both the communication tube 200 and the needle.

Subsequently, the injection solution in the syringe 400 should be exactly injected into a functional tissue of the ovary 500. Although the ovary 500, the vagina, and the uterus are near the rectum 501, they can be easily discriminated from one another by touch. For example, when the finger is inserted into the rectum 501 of a female animal and the rectum is pressed downward, the ovary 500 can be palpated as being firm to the touch. If he or she grasps and pulls the ovary outwardly with the palm hollowed, a proximal arrangement is formed among the fingers, the rectum wall, the ovary and the vagina wall as shown in FIG. 1. In this state, when the catheter 100 is inserted into the vagina 202 and the front end of the catheter 100 is lifted upwardly, the operator can detect that that the front end of catheter 100 is positioned immediately beneath the ovary 500. Under these conditions, the communication tube 200 that protrudes in the rear direction is moved forward by pushing, and the motion is blocked to extend the needle 203 to a proper length as the circumferential part of the needle 203 reaches the stopper 101. Hence, the needle 203 extends from the front end of the catheter 100 and penetrates through the vaginal wall into the functional tissue of the ovary 500. At this time, pressing the thumb rest 402 of the syringe 400 allows the injection solution in the syringe 400 to pass through the communication tube 200 and then to be projected from the needle 203 into the functional tissue of the ovary 500.

After the injection solution loaded to the syringe 400 is injected into the functional tissue of the ovary, the device is extracted from the vagina 500, with the catheter 100 held by one hand, and then the fingers of the other hand are withdrawn from the rectum 501.

Once the injection solution is applied to a functional tissue of the ovary, it causes ovarian dysfunction. The injection solution is a composition comprising 10% to 90% by weight of lactic acid and 10% to 90% by weight of an adjuvant, and having a pH of 1~5.

Example 1

As an injection solution for inducing ovarian dysfunction, a composition, with a pH of 2, comprising 20% by weight of lactic acid and 80% by weight of the adjuvant phosphate buffered saline was injected at a dose of 5 ml into a functional tissue of the ovary.

Figure 2:
FIG. 2 is an image of a cow ovary.

A pre-injection ovary is shown in FIG. 2.

Figure 3:
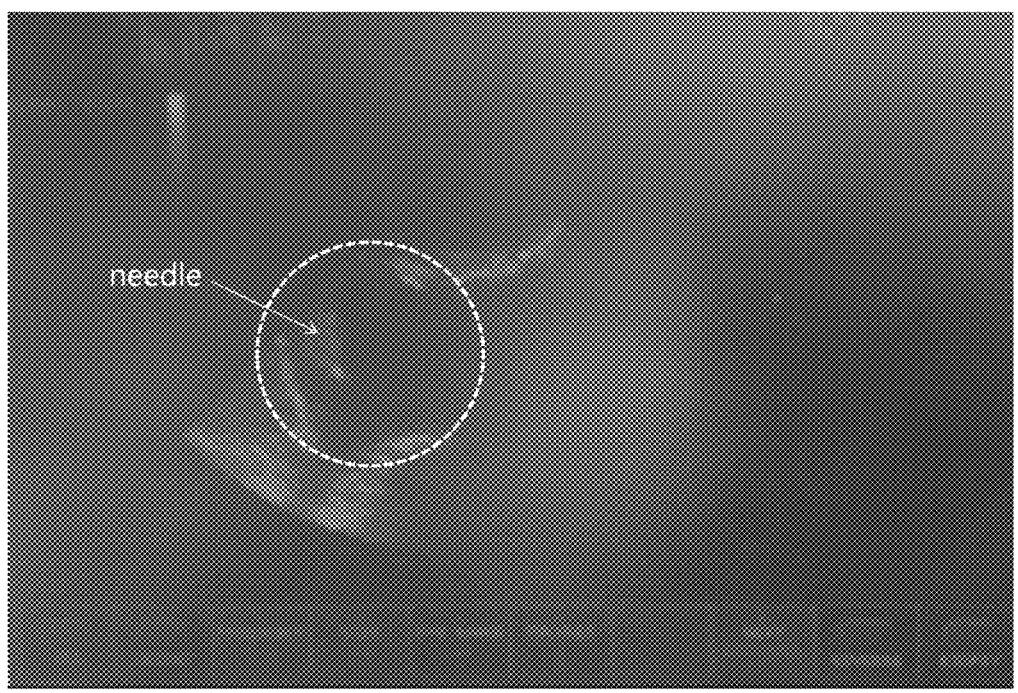
FIG. 3 is an image of a cow ovary into which a needle is penetrated.
Figure 4:
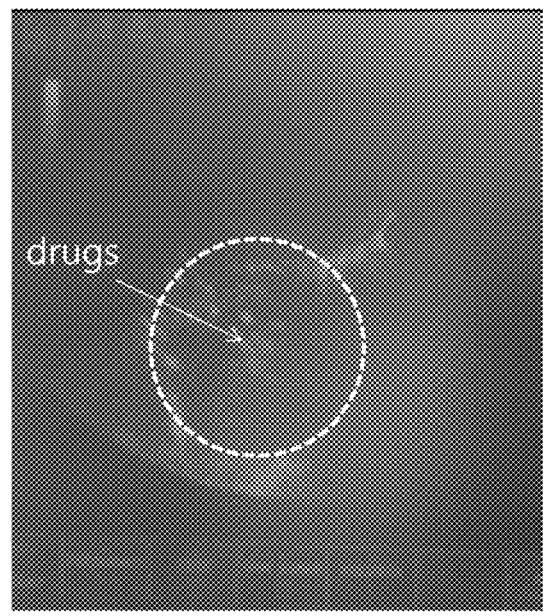
FIG. 4 is an image of an ovarian tissue in which an injection solution is dispersed by injection.

FIG. 3 shows functional ovarian tissue to which a needle has penetrated in the procedure described above, and FIG. 4 shows functional ovarian tissue to which the injection solution has been injected via the needle.

Figure 5:
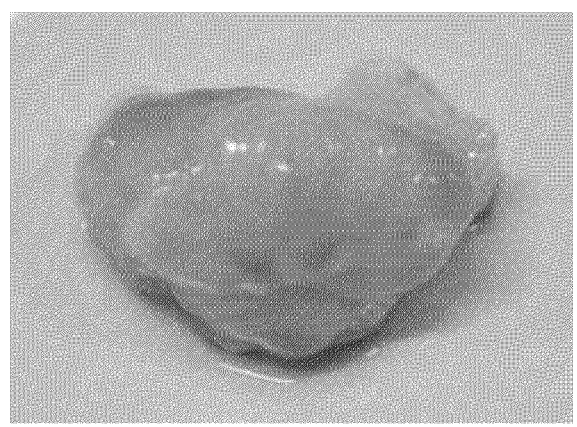
FIG. 5 is an image of an ovary from a control not injected with the composition of Example 1.
Figure 6:
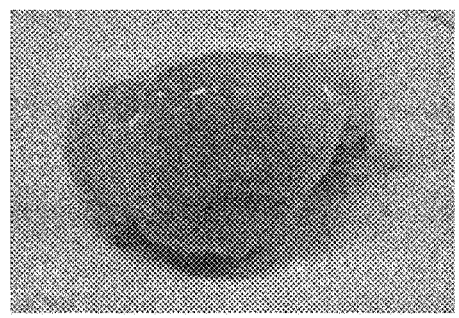
FIG. 6 is an image of a test group injected with the composition of Example 1.

The cow was butchered to excise the ovarian tissue 30 days after the application of the injection solution to the ovarian tissue. The ovarian tissue of the cow was found to undergo a color change from the color hex code #CC3D3D to the color hex code #CCA63D, relative to a control, as compared to FIGS. 5 and 6.

Color hex code #CC3D3D in control

RGB 2046161

Color hex code #CCA63D

RGB 20416661

In addition, the ovarian tissue injected with the composition measured 21.3 mm in diameter, which was reduced by 18%, compared to that of the control, 26 mm in size.

The composition was examined for ability to induce ovarian dysfunction. In this regard, the composition was injected into 14 test cows. Of them, 13 were anestrous for 3 months, with only one being on heat. The results are summarized in Table 1, below.

Considering the fact that a cow has an estrus cycle of 21 days on average, all the test cows, except one, had been maintained as being completely anestrous for 3 months or longer after the injection (Jul. 30, 2013), with an efficiency of as high as 93%.

TABLE 1

| Group | ID. No. | Birth Date | Wt. on testing | Remark |
|---|---|---|---|---|
| Control | 300722735 | 2012 Sep. 6 | 250 | With an estrus cycle of 21 |
| | 300699598 | 2012 Aug. 23 | 260 | |
| | 300722743 | 2012 Sep. 9 | 233 | |
| | 300014294 | 2012 Jun. 9 | 289 | |
| | 082784030 | 2012 Nov. 30 | 193 | |
| | 082784048 | 2012 Dec. 20 | 165 | |
| | 300717339 | 2012 Nov. 2 | 223 | |
| | 300717347 | 2012 Nov. 7 | 200 | |
| | 300722794 | 2012 Oct. 26 | 203 | |
| | 075364894 | 2012 Mar. 4 | 458 | |
| | 300014059 | 2012 Apr. 14 | 432 | |
| | 075364886 | 2012 Mar. 1 | 417 | |
| | 075364843 | 2012 Feb. 21 | 417 | |
| | 300013912 | 2012 Mar. 25 | 416 | |
| | 075364992 | 2012 Mar. 10 | 410 | |
| Test | 300699580 | 2012 Aug. 17 | 254 | Anestrous until November, 2013 |
| | 300699602 | 2012 Aug. 23 | 279 | Anestrous until November, 2013 |
| | 300699571 | 2012 Aug. 20 | 282 | Anestrous until November, 2013 |
| | 300699547 | 2012 Aug. 16 | 236 | Anestrous until November, 2013 |
| | 300719424 | 2012 Aug. 27 | 273 | Anestrous until November, 2013 |
| | 300699539 | 2012 Aug. 19 | 270 | Anestrous until November, 2013 |
| | 300014286 | 2012 May 29 | 330 | Anestrous until November, 2013 |
| | 300014219 | 2012 Jun. 1 | 312 | Anestrous until November, 2013 |
| | 300014018 | 2012 Apr. 10 | 374 | Anestrous until November, 2013 |
| | 300014260 | 2012 May 16 | 336 | Anestrous until November, 2013 |
| | 300014042 | 2012 Apr. 11 | 370 | Anestrous until November, 2013 |
| | 300013904 | 2012 Mar. 24 | 391 | Anestrous until November, 2013 |
| | 75365008 | 2012 Mar. 9 | 388 | Being in heat on August 17 |
| | 300014075 | 2012 Apr. 8 | 396 | Anestrous until November, 2013 |

To the test group, an injection solution containing 20% by weight of lactic acid was injected on Jul. 30, 2013.

Figure 7:
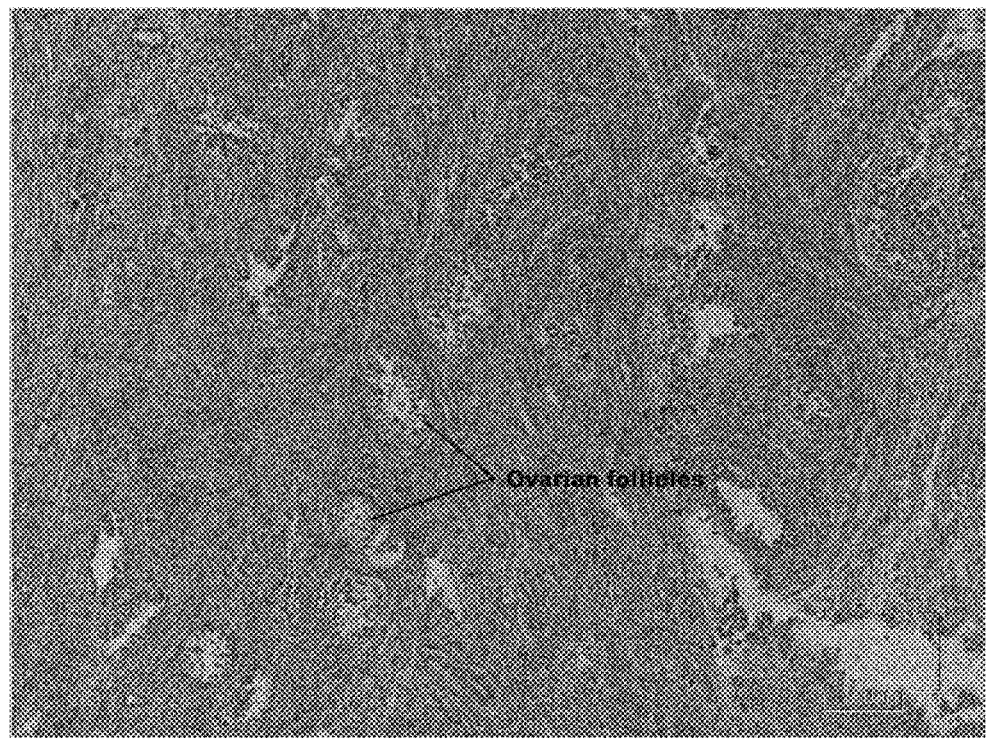
FIG. 7 is a histological image of an ovary from a normal control (H-E staining)
Figure 8:
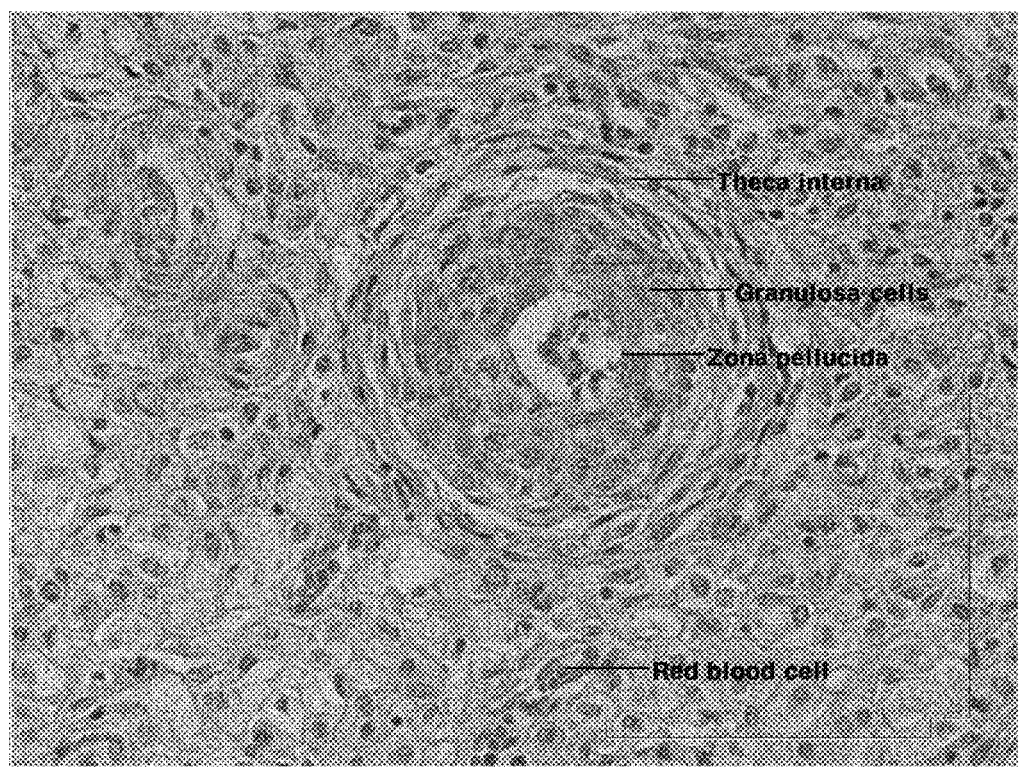
FIG. 8 is a histological image of ovarian follicles growing in a normal bovine ovarian tissue (H-E staining).

Ovarian tissues from the control cows that were not injected with the lactic acid composition were taken as permanent preparations and observed under an optical microscope. As shown in FIGS. 7 and 8, an ovarian follicle, also called multilaminar primary follicle or preantral follicle, in which liquor folliculi was not sufficiently accumulated, appeared to grow. Also, granulosa cells that proliferated as a result of the mitosis of follicular cells were observed, but with theca interna only.

Figure 9:
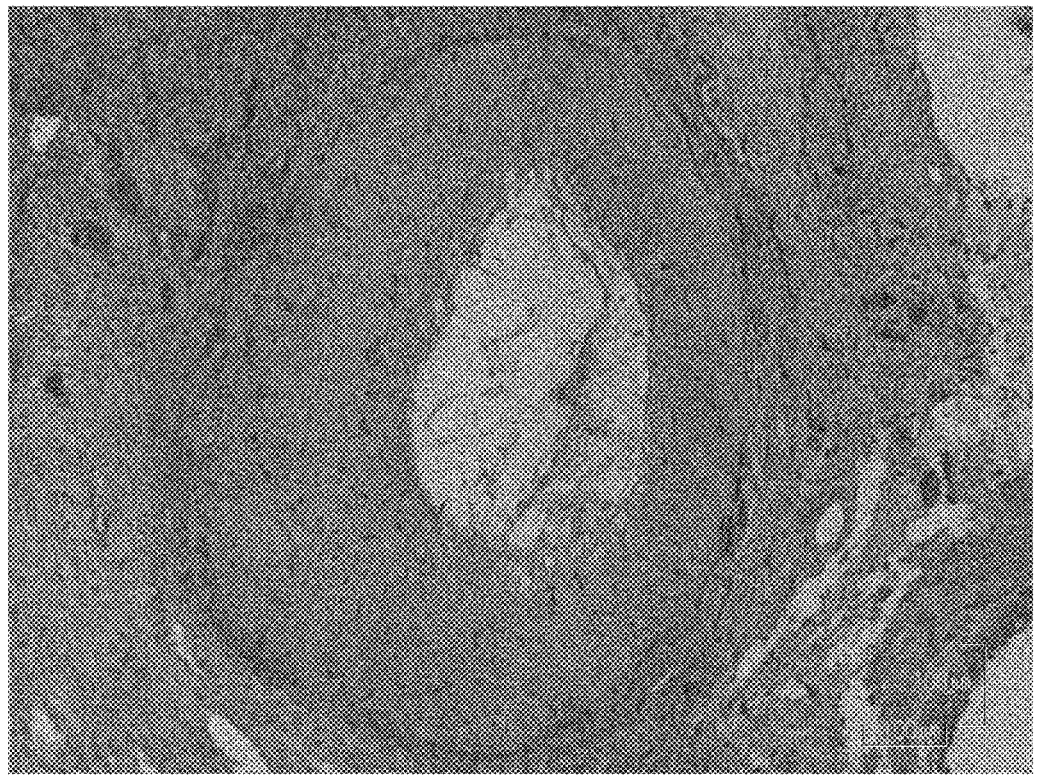
FIG. 9 is an image of an ovarian tissue treated with lactic acid (H-E staining)
Figure 10:
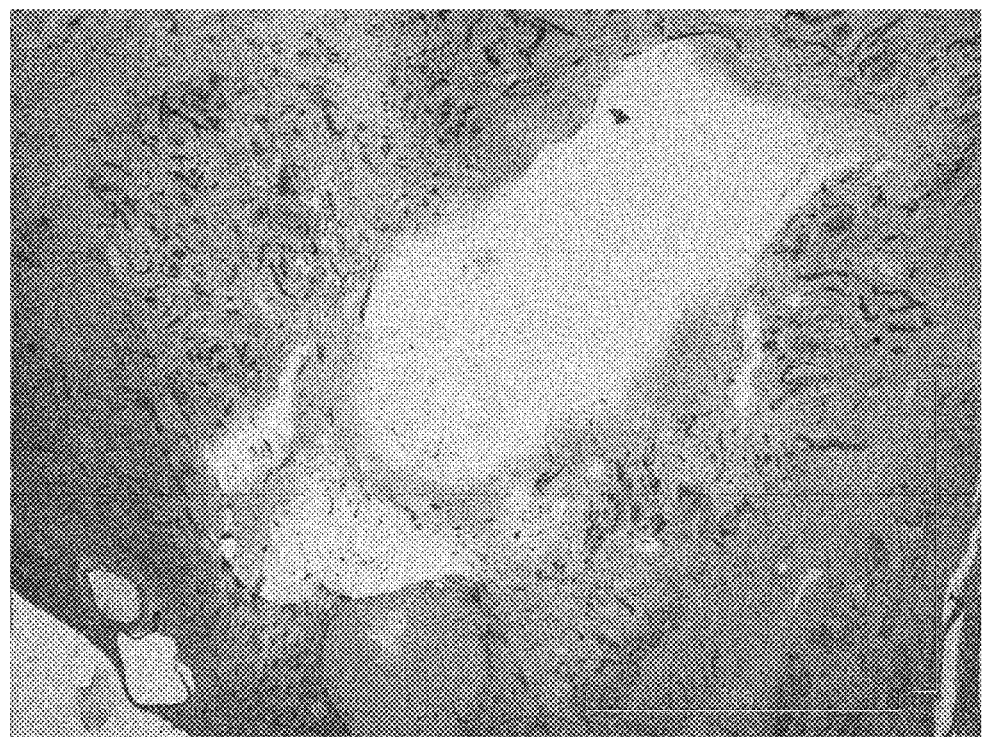
FIG. 10 is an image of the ovarian tissue of FIG. 9, at 1/10 magnification (H-E staining)

The bovine ovarian tissues shown in FIGS. 7 and 8 were significantly different in histology from those shown in FIGS. 9 and 10, which were taken from the test group treated with lactic acid. The most different was that no certain morphologies were found in the cells of the test group (see FIG. 9).

For ovarian follicles, no nuclei were found in granulose cells, and membrane borders of cells adjacent to the ovarian follicles were difficult to discriminate. Further, follicular cells that were developed in the ovarian tissues were observed to have no normal morphologies. These observations demonstrated that treatment with lactic acid incurred the necrosis of ovarian cells.

Example 2

As an injection solution for inducing ovarian dysfunction, a composition, with a pH of 1.4, comprising 40% by weight of lactic acid and 60% by weight of deionized water was injected at a dose of 4 ml into a functional tissue of the ovary.

Figure 11:
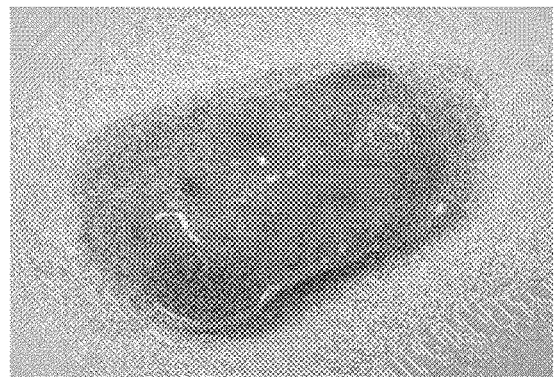
FIG. 11 is an image of an ovary from a control that has not been injected with the composition of Example 2.
Figure 12:
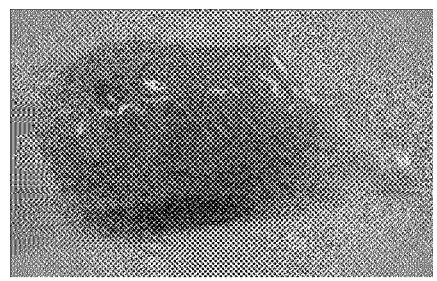
FIG. 12 is an image of an ovary from a test group that has been injected with the composition of Example 2.

A color change from color hex code #F15F5F to #F2CB61 was detected in the ovarian tissue of the cow injected with the composition, as shown in FIGS. 11 and 12.

Pre-injection:#F15F5F

RGB 2419595

Post-injection: #F2CB61

RGB 24220397

In addition, the ovarian tissue injected with the composition measured 17.3 mm in diameter, which was reduced by about 28%, compared to that of the control, 24 mm in size.

The composition was examined for ability to induce ovarian dysfunction. In this regard, the composition was injected into 5 test cows. All of them were anestrous for 3 months. The results are summarized in Table 2, below. Considering the fact that a cow has an estrus cycle of 21 days on average, all the test cows had been maintained as being completely anestrous for 3 months or longer after the injection, with an efficiency of 100%.

TABLE 2

| Group | ID. No. | Birth Date | Wt. on testing | Remark |
|---|---|---|---|---|
| Test | 300014333 | 2012 Aug. 7 | 287 | Anestrous until November, 2013 |
| | 300014405 | 2012 Aug. 11 | 283 | Anestrous until November, 2013 |
| | 300014294 | 2012 Jun. 11 | 282 | Anestrous until November, 2013 |
| | 070764039 | 2012 Feb. 5 | 398 | Anestrous until November, 2013 |
| | 075364851 | 2012 Feb. 21 | 389 | Anestrous until November, 2013 |

To the test group, THE was injected on Jul. 30, 2013.

Example 3

As an injection solution for inducing ovarian dysfunction, a composition, with a pH of 2.8, comprising 30% by weight of lactic acid and 30% by weight of the adjuvant protein buffer was injected at a dose of 4 ml into a functional tissue of the ovary. In addition, the ovarian tissue injected with the composition measured 14.3 mm in diameter, which was reduced by about 35%, compared to that of the control, 22 mm in size.

The composition was examined for ability to induce ovarian dysfunction. In this regard, the composition was injected into 4 test cows. All of them were maintained to be anestrous for 9 months until butchery. The results are summarized in Table 3, below. Considering the fact that a cow has an estrus cycle of 21 days on average, all the test cows had been maintained as being completely anestrous for 9 months or longer after the injection, with an efficiency of 100%. Moreover, the test group was measured to gain greater weight than the control.

TABLE 3

| Group | ID No. | Birth Date | Wt. on testing | Wt. on Butchery | Wt. gain | Remark |
|---|---|---|---|---|---|---|
| Control | 000150169631 | 2000 Feb. 19 | 489 | 568 | 79 | Regularly estrous |
| | 000195287477 | 2006 Aug. 23 | 586 | 634 | 48 | " | until butchery |
| | 000195286517 | 2006 Mar. 10 | 550 | 590 | 40 | " | on May 5, 2013 |
| Test | 000155733861 | 2000 Mar. 1 | 396 | 542 | 146 | Anestrous |
| | 000150163576 | 2000 Aug. 15 | 533 | 676 | 143 | until butchery |
| | 002008358812 | 2007 Aug. 19 | 428 | 530 | 102 | on May 5, 2013 |
| | 000150163691 | 2000 Aug. 13 | 416 | 512 | 96 | |

To the test group, THE was injected on Jul. 5, 2012.

When injected into a functional tissue of the ovary in this Example, the lactic acid-containing composition for inducing ovarian dysfunction according to the present invention caused tissue necrosis and acidification. The lactic acid injected is decomposed to carbon dioxide and water, which are non-toxic, so that the composition can increase the production of safe meat.

The adjuvants, phosphate buffer, deionized water and protein buffer, used in Examples 1 to 3, were used to stabilize the pH of the composition. Alternatively, other adjuvants may be employed to guarantee the stable performance of the composition of the present invention so long as they are safe.

INDUSTRIAL APPLICABILITY

Although the preferred embodiment(s) of the present invention have (has) been disclosed for illustrative purposes, those skilled in the art will appreciate that various modifications, additions and substitutions are possible, without departing from the scope and spirit of the invention as disclosed in the accompanying claims.

The invention claimed is:

1. A system for inducing ovarian dysfunction, comprising:
  a) a composition comprising:
    10% to 90% by weight of lactic acid, sodium lactate, calcium lactate, or a mixture thereof; and
    10% to 90% by weight of an adjuvant, wherein the adjuvant is a phosphate buffer or a protein buffer,
    wherein the composition has a pH of between 1 and 5; and
  b) an injector adapted to inject said composition into an ovary.

2. The system of claim 1, comprising 10% to 90% by weight of lactic acid and 10% to 90% by weight of said adjuvant.

3. The system of claim 1, comprising 10% to 90% by weight of sodium lactate and 10% to 90% by weight of said adjuvant.

4. The system of claim 1, comprising 10% to 90% by weight of calcium lactate and 10% to 90% by weight of said adjuvant.

5. The system of claim 1, wherein the adjuvant is a protein buffer.

6. A system for inducing ovarian dysfunction, comprising:
  a) a composition comprising:
    10% to 90% by weight of lactic acid, sodium lactate, calcium lactate, or a mixture thereof; and
    10% to 90% by weight of an adjuvant,
    wherein the adjuvant is a phosphate buffer,
    wherein the composition has a pH of between 1 and 5; and
  b) an injector adapted to inject said composition into an ovary.

* * * * *